US007658737B2

(12) United States Patent
Hartlaub et al.

(10) Patent No.: US 7,658,737 B2
(45) Date of Patent: Feb. 9, 2010

(54) METHOD AND APPARATUS TO SENSE TEMPERATURE IN AN IMPLANTABLE PUMP

(75) Inventors: Jerome T. Hartlaub, New Brighton, MN (US); James M. Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 640 days.

(21) Appl. No.: 09/950,154

(22) Filed: Sep. 10, 2001

(65) Prior Publication Data

US 2002/0042596 A1    Apr. 11, 2002

Related U.S. Application Data

(63) Continuation-in-part of application No. 09/302,517, filed on Apr. 30, 1999, now abandoned.

(51) Int. Cl.
*A61K 9/22* (2006.01)
*F04B 49/10* (2006.01)
*F04B 49/00* (2006.01)
*G01K 1/00* (2006.01)
*G01K 1/08* (2006.01)
*G01K 3/00* (2006.01)
*G01K 5/00* (2006.01)
*G06F 17/18* (2006.01)
*G06F 19/00* (2006.01)
*G21C 17/00* (2006.01)

(52) U.S. Cl. .................. 604/891.1; 417/32; 417/63; 702/130; 702/132; 702/179; 702/182

(58) Field of Classification Search .............. 604/93.01, 604/500, 503, 95.01, 131, 288.04, 890.1–890.2, 604/891.1, 892.1; 374/100, 141; 600/300; 705/2; 417/32, 63; 702/130, 132, 179, 182
See application file for complete search history.

(56) References Cited

U.S. PATENT DOCUMENTS

| | | | |
|---|---|---|---|
| 4,403,984 A | | 9/1983 | Ash et al. |
| 4,627,840 A | * | 12/1986 | Cuadra et al. ............... 604/151 |
| 5,115,811 A | | 5/1992 | Hartlaub et al. |
| 5,309,919 A | * | 5/1994 | Snell et al. .................. 600/510 |
| 5,556,421 A | | 9/1996 | Prutchi et al. |
| 5,593,430 A | | 1/1997 | Renger |
| 5,676,651 A | * | 10/1997 | Larson et al. ................. 604/33 |
| 5,730,720 A | | 3/1998 | Sites et al. |
| 5,904,708 A | * | 5/1999 | Goedeke ....................... 607/18 |
| 6,016,447 A | | 1/2000 | Juran et al. |
| 6,176,822 B1 | * | 1/2001 | Nix et al. ...................... 600/17 |
| 6,280,416 B1 | * | 8/2001 | Van Antwerp et al. ....... 604/141 |

\* cited by examiner

*Primary Examiner*—Matthew F DeSanto
(74) *Attorney, Agent, or Firm*—Scott A. Marks

(57) ABSTRACT

An implantable drug infusion pump for delivering drug therapy is made more reliable and its performance improved by monitoring drug pump temperature. Monitoring pump temperature can also provide for temperature-related drug therapy modification.

A pump temperature sensor is read by the infusion pump's microprocessor. Pump temperature data is stored in pump memory for later access by a remote controller. A simple thermistor or semiconductor temperature sensor can provide fast and reliable temperature monitoring of the pump and/or of a patient by reading the temperature sensor's value and calculating a temperature therefrom.

19 Claims, 8 Drawing Sheets

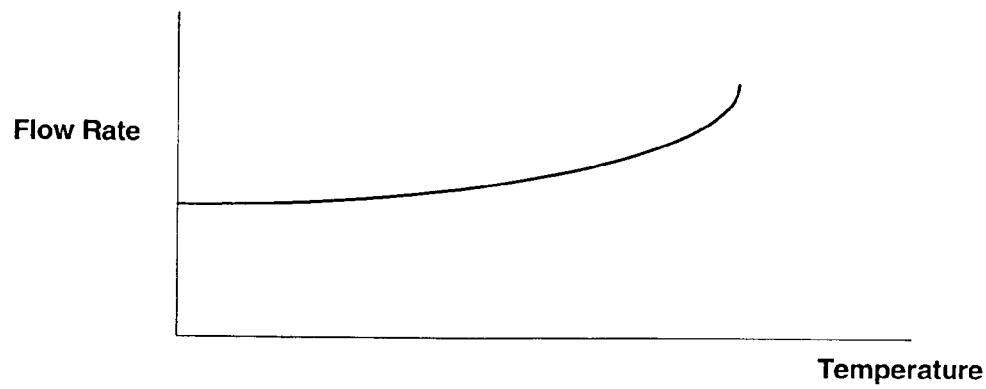
FIGURE 4A - Uncompensated Flow Rate
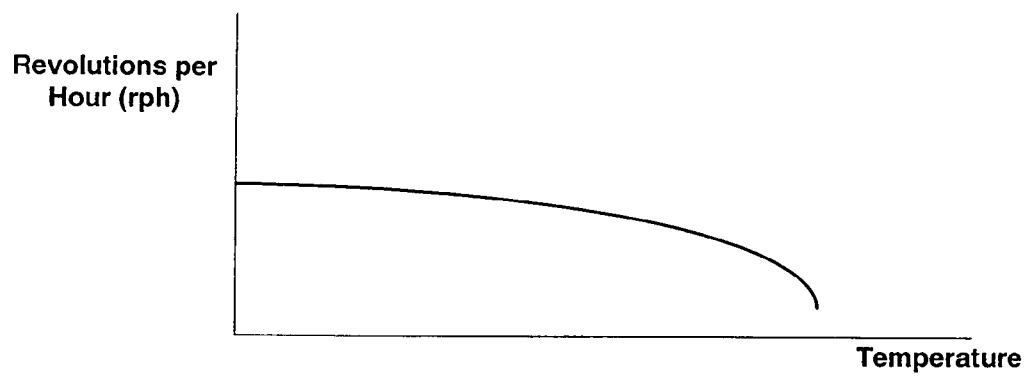
FIGURE 4B - Temperature Compensation Algorithm
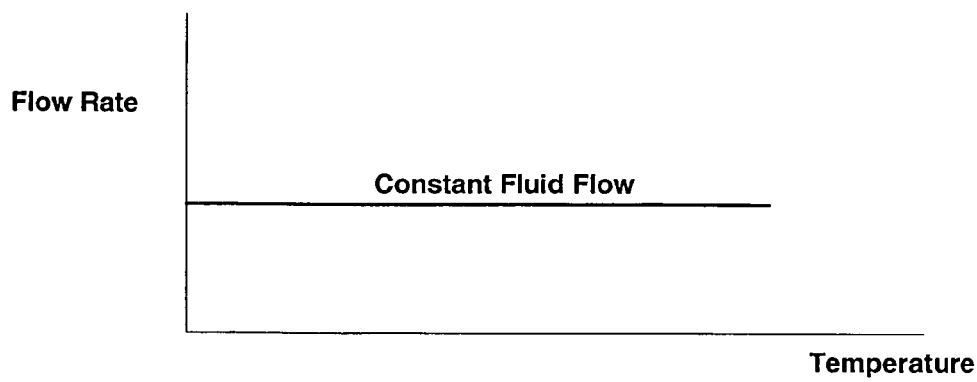
FIGURE 4C - Temperature Compensated Flow Rate

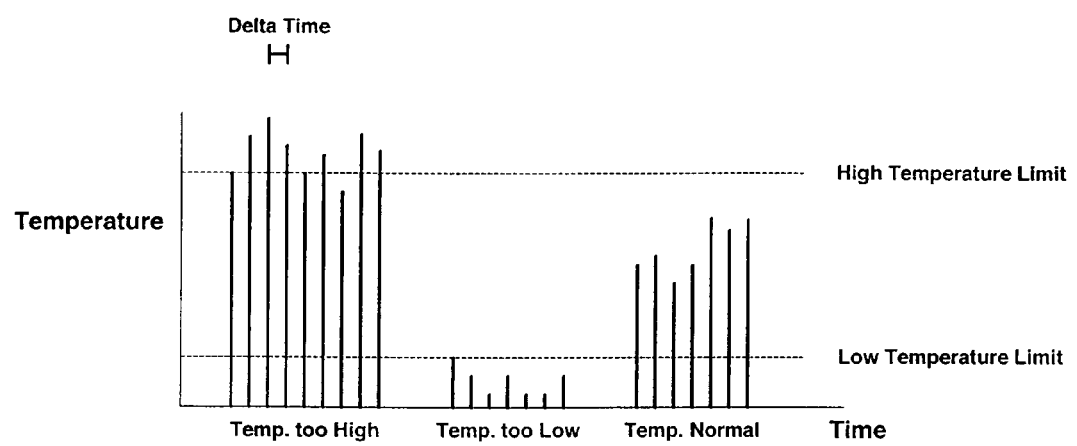
FIGURE 5A - Pump Temperature Samples
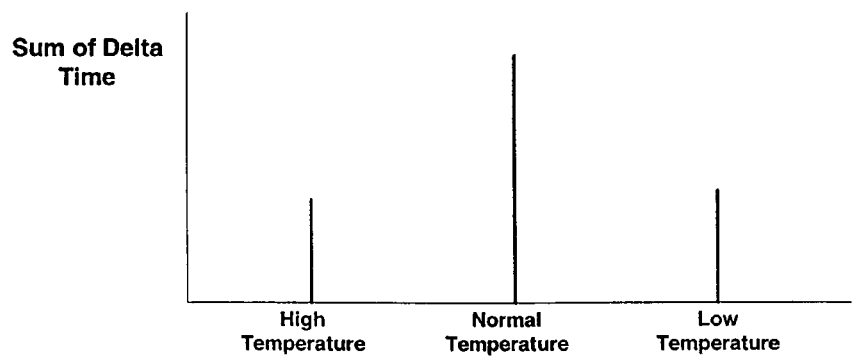
FIGURE 5B - Histogram Output

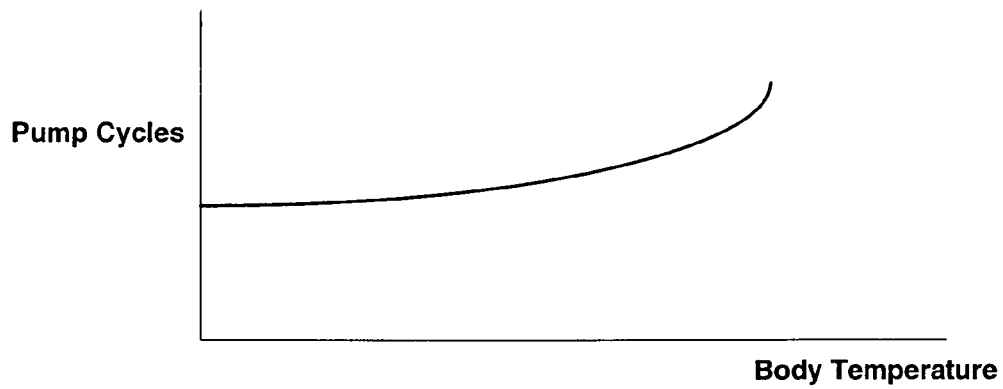
FIGURE 7A - Pump Cycles vs. Body Temperature
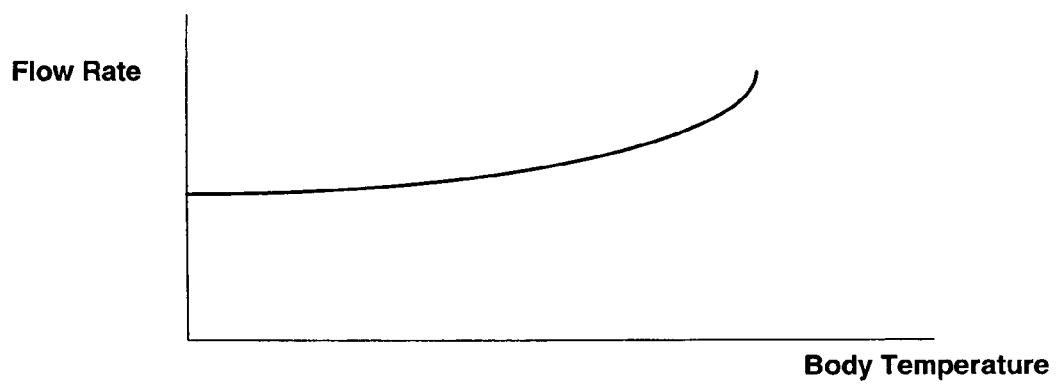
FIGURE 7B - Flow Rate vs. Body Temperature

"METHOD AND APPARATUS TO SENSE TEMPERATURE IN AN IMPLANTABLE PUMP"

This is a continuation-in-part application of U.S. patent application Ser. No. 09/302,517, filed Apr. 30, 1999, now abandoned, for which priority is claimed.

FIELD OF THE INVENTION

This invention relates to implantable drug infusion pumps. In particular, this invention relates to a method and apparatus for continuously sensing and recording temperature of an implantable infusion pump.

BACKGROUND OF THE INVENTION

Implanted infusion pumps deliver therapeutic drugs to a patient according to a computer program executed by a processor that is programmed with drug dosing parameters. Some infusion pumps use a microprocessor to control a small, positive displacement pump according to programming instructions delivered to the microprocessor through an RF programming link so as to permit the implantable pump to be remotely programmed and operated. Other infusion pumps use compressed-gas propellants instead of a pump to deliver a drug.

Most medical devices, including infusion pumps, are specified to be stored in a particular not-to-be-exceeded temperature range. Storage temperatures outside the manufacturer's specified storage temperature range can damage implantable infusion pumps and for this reason, precautions are normally taken to insure that an implantable infusion pump is not inadvertently subjected to adversely high or low temperatures. Monitoring a pump's temperature over time would provide a mechanism by which damaging temperature extremes could be identified prior to implantation.

In addition, a pump that includes a mechanism by which the pump's temperature can be monitored might provide drug-delivery performance improvements. The flow characteristics of mechanical pumps are often temperature sensitive. Temperature compensation of undesirable flow changes can be achieved using the electrical temperature signal to adjust the flow via the internal controller.

Furthermore, monitoring patient temperature by an infusion pump, either remotely, for example at the distal end of a catheter connected to the pump, or at the pump, might allow for drug therapy delivery to be modified according to the patient's measured temperature, improving the effectiveness of the therapy.

BRIEF SUMMARY OF THE INVENTION

An implantable drug infusion pump is made more reliable and its performance is improved by inclusion of a temperature sensor in the pump, which monitors the pump's temperature. Undesirable temperature dependencies in an infusion pump's performance can be reduced or eliminated by measuring the pump's actual temperature using a separate temperature sensor and adjusting the pump's operation accordingly by way of a computer program designed to modify pump performance according to temperature variations. Drug therapy administered by an infusion pump can be automatically or manually adjusted according to the pump's actual temperature.

In the preferred embodiment, a thermistor, embedded within a pump at an empirically determined optimum location to monitor the overall temperature of the pump's constituent mechanisms, is operatively coupled to the pump's control microprocessor. The microprocessor's control program is written to read the thermistor's resistance and from the temperature-dependent resistance of the thermistor, calculate the pump's temperature.

In at least one alternate embodiment, a temperature sensor external to the infusion pump can be used to measure a patient's temperature. Such an embodiment would include using a temperature sensing device, on the distal end of a catheter for example, providing a faster temperature sensor and a temperature more closely similar to the core temperature of a patient.

EEPROM or battery-powered RAM, on-board the microprocessor or in an external device, can be used to store the date and time at which a microprocessor controlling the pump and also monitoring a temperature probe, read the pump's temperature. The microprocessor can correlate an electrically measurable parameter, such as a temperature-dependent resistance of a thermistor for example, to a real temperature. The pump's temperature-history since manufacture and prior to implant into a patient can be stored in memory and subsequently read from memory thereby providing a complete history of the pump's temperature. Historical temperatures stored and read prior to installation might help insure that the pump will not fail due to having been frozen or fail because of exposure to abnormally high temperatures since manufacture, causing a possible electrical or mechanical failure.

Pump temperature data values stored in memory can be read from the pump prior to installation using a direct-connect-programming link or through a RF programming link, which is commonly used to transfer data to and from implantable infusion pumps and described elsewhere in the literature. See e.g. U.S. Pat. No. 4,676,248, "Circuit for Controlling a Receiver in an Implanted Device" by Berntson.

BRIEF DESCRIPTION OF THE DRAWINGS

FIG. 4A shows a graph of an uncompensated flow rate of an implantable pump versus temperature.

FIG. 4B shows a graph of a temperature compensation algorithm's programmed relationship between pump revolutions per hour for an implantable pump and temperature.

FIG. 4C shows a graph of a temperature compensated flow rate of an implantable pump.

FIG. 5A shows the temperature profile of an implantable pump over time.

FIG. 5B shows the histogram output of the total time an implantable pump was exposed to various temperature ranges.

FIG. 7A shows a graph of an implantable pump's pump cycles verses a patient's body temperature.

FIG. 7B shows a graph of flow rate of an implantable pump versus a patient's body temperature.

DETAILED DESCRIPTION OF THE INVENTION

Figure 1:
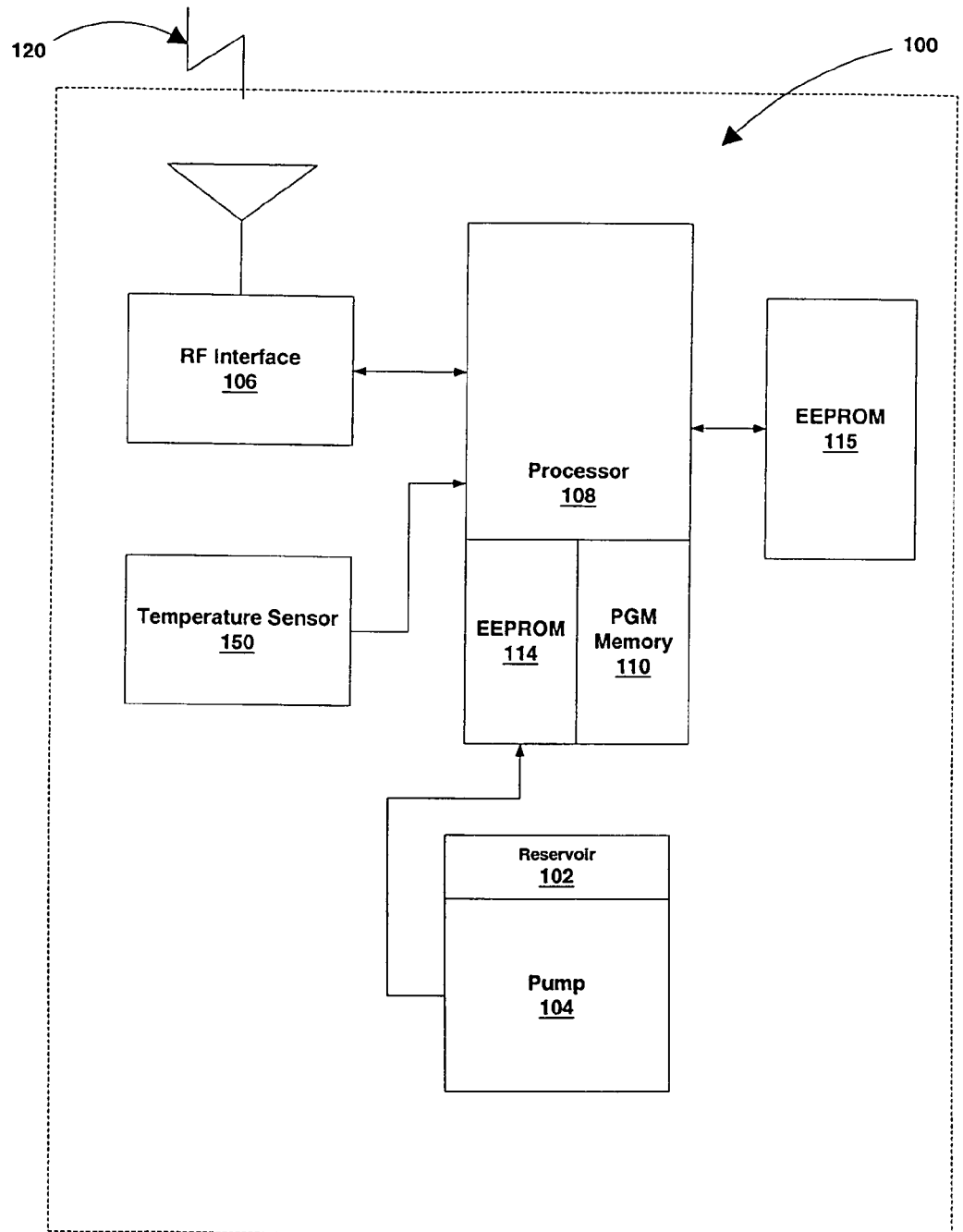
FIG. 1 discloses a simplified block diagram of an implantable, software controlled infusion pump that also includes a built-in temperature sensor.

FIG. 1 shows a simplified block diagram of the functional elements of an implantable and programmable drug infusion pump 100 having a programmable microprocessor 108 and a temperature sensor 150 for monitoring the pump temperature.

The functional elements of the infusion pump 100 are shown in FIG. 1 are small, such that the pump can be readily implanted into the abdomen of a patient for purposes of treating chronic diseases, such as diabetes. An implanted infusion pump might also be used for acute treatment regimens, e.g. to administer chemotherapy drugs or morphine, for example. A reservoir 102 contains a volume of drug to be administered to the patient by a pump 104, preferably a precision positive displacement pump controlled by the microprocessor 108 and drawing drug material from the reservoir 102.

The pump 104 shown in FIG. 1 is operatively coupled to and responsive to electrical signals delivered to it from a radio frequency (RF) interface unit 106. Electrical signals from the interface unit 106 might, for example, start and stop the pump 104 and including its delivery rate so as to modulate the delivery of drugs from the reservoir 102 to the patient. Control circuitry within the microprocessor unit 108 would typically include appropriate electronic drive circuits, the essential function of which is to couple a central processor 108 to the pump 104 through appropriate interface circuitry well know to those skilled in the art. Alternate embodiments of the invention would of course include implementing any required pump/CPU interface directly into the microprocessor, or selecting and/or designing the pump 104 to eliminate the need for an interface between it and the low power circuits of the microprocessor. Many commercial grade microprocessors include a plethora of ancillary circuitry on a single substrate including analog-to-digital converters, digital-to-analog converters, counters, timers, clocks and so forth.

The central processor unit 108 controls the amount of drug treatment administered to the patient according to program instructions stored in a program memory 110. In the case of a displacement pump mechanism, the microprocessor might control a drive motor's speed as well as its "on" time.

A temperature sensor 150 is operatively coupled to at least one input of the microprocessor 108. The preferred embodiment of the invention contemplates that the temperature sensor is a thermistor, the resistance of which varies with the temperature of the thermistor. Many single-chip microcontrollers are fabricated to include an analog-to-digital converter which might be employed to measure the resistance of the thermistor by the microcontroller thereby reducing parts count. In using an on-chip circuit to measure the thermistor's temperature, the control program of the microcontroller can correlate the thermistor's resistance to a temperature, indirectly measuring temperature by the thermistor's resistance. Alternate embodiments of the invention would include using a temperature sensor that is a semiconductor for it is well known that semiconductor performance characteristics are affected by temperature. A semiconductor temperature sensor might be fabricated directly on the same die as the microprocessor.

Figure 2:
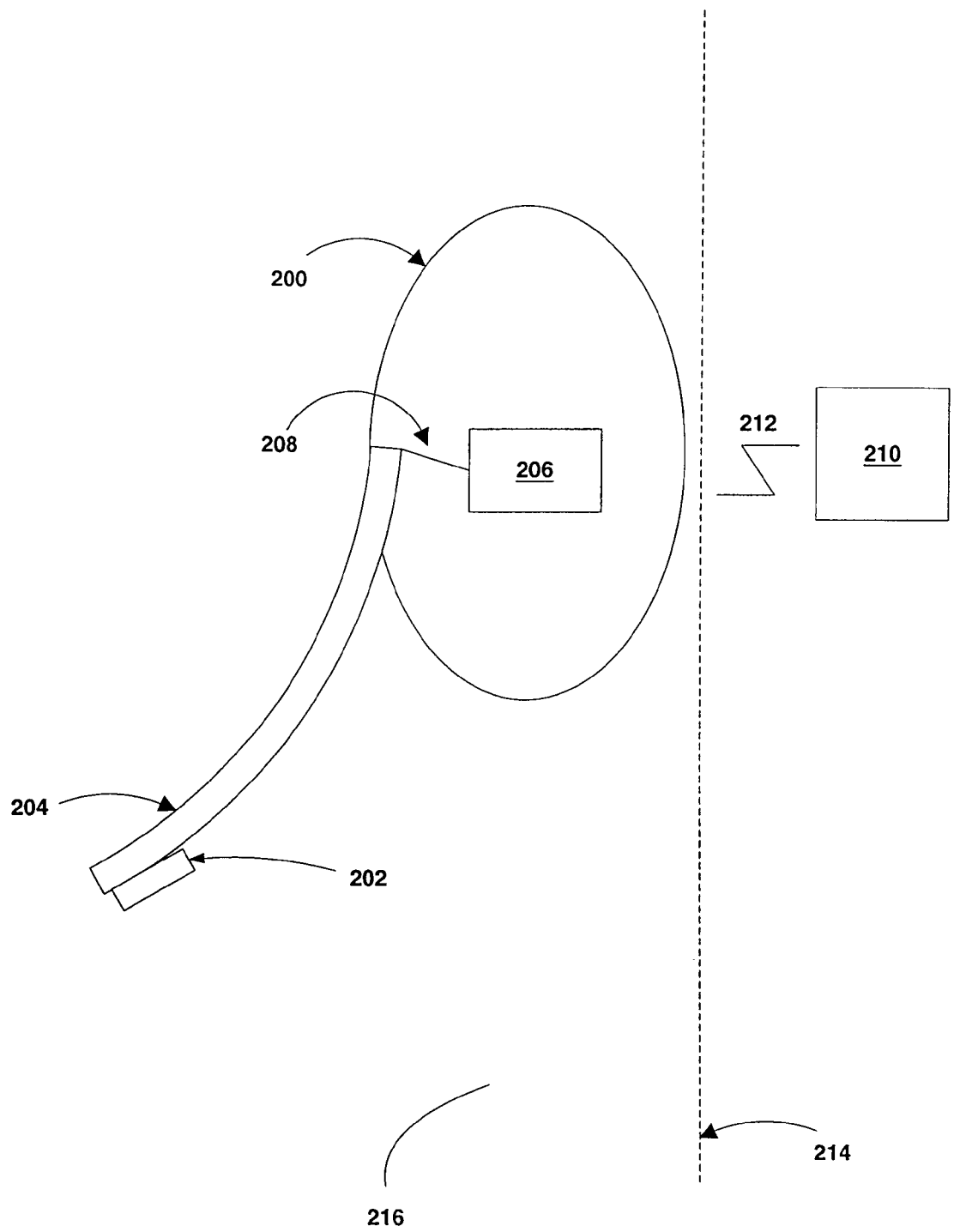
FIG. 2 shows an alternate embodiment wherein a catheter includes a temperature sensor coupled to a pump, which might include an external controller.

Still other embodiments of the invention would include a pump that senses temperature through a remote temperature probe. FIG. 2 shows an alternate embodiment of a temperature-sensing infusion pump 200 wherein a temperature sensor 202 is affixed to the distal end of a catheter 204 and electrically coupled to a pump or its microprocessor 206 through appropriate-small gauge wire 208. Such a device might be used to sense a patient's temperature, separate and apart from the pump's temperature remotely from the pump but still within the patient's body, or in addition to the pump's temperature for purposes of varying drug dosage according to the patient's temperature.

The pump 200 with the catheter 204 connected are implanted in the patient's body 216 under the skin 214. For remote programming purposes, RF energy 212 flows bidirectionally between the pump 200 and the external controller 210 as is commonly done in the art.

Monitoring the pump's temperature over time means that the microprocessor's 108 control program might periodically scan or read the resistance of the thermistor or other temperature sensing device. Temperature data values read from the temperature sensor might be stored in memory to be read out or analyze at a later time. Alternatively, temperatures that are read and which are outside an acceptable temperature range limit can be selectively stored reducing the amount of data that might need subsequent analysis. In other words, only temperatures that are too high or too low might be stored in memory for later analysis.

Data read from the temperature sensor can be stored in EPROM 114. EEPROM 114 is particularly useful in the invention as it readily lends itself as a repository for long-term data storage regardless of whether or not power to the memory device has been supplied continuously or interrupted. Many commercially available microprocessors include addressable EEPROM directly on the substrate comprising the CPU further simplifying the implementation of a software-limited dosage implantable drug infusion device. Alternate embodiments of the invention for storing temperature data include internal RAM memory or would external EEPROM, such as the memory device identified by reference numeral 115.

Historical data of the pump's temperature might be read from the pump using the RF programming link 212. Appropriate instruction to the microprocessor would cause the microprocessor to read and transfer for uploading one or more of the data values stored in EEPROM, RAM or other data storage device. A complete record of the pump's temperature from its manufacture could be re-created providing some assurance that the pump had not been subjected to a damaging temperature extreme.

By use of the invention disclosed herein, the storage temperature history of an implantable infusion pump over time might help identify pumps that are likely to fail after installation. Implantable pumps have a specified storage temperature range over which the implantable pump can be stored safely and continue to be suitable for patient implantation. If the pump is exposed to a higher or lower temperature than the storage temperature limit permits, it is possible for the pump to be damaged and not function as designed. Thus, it is desirable that the healthcare provider be aware of historical temperatures that an implantable pump has been exposed to prior to implant. If the implantable pump has been exposed to temperature damaging extremes, the healthcare provider can decide not to implant the pump into the patient.

Figure 6:
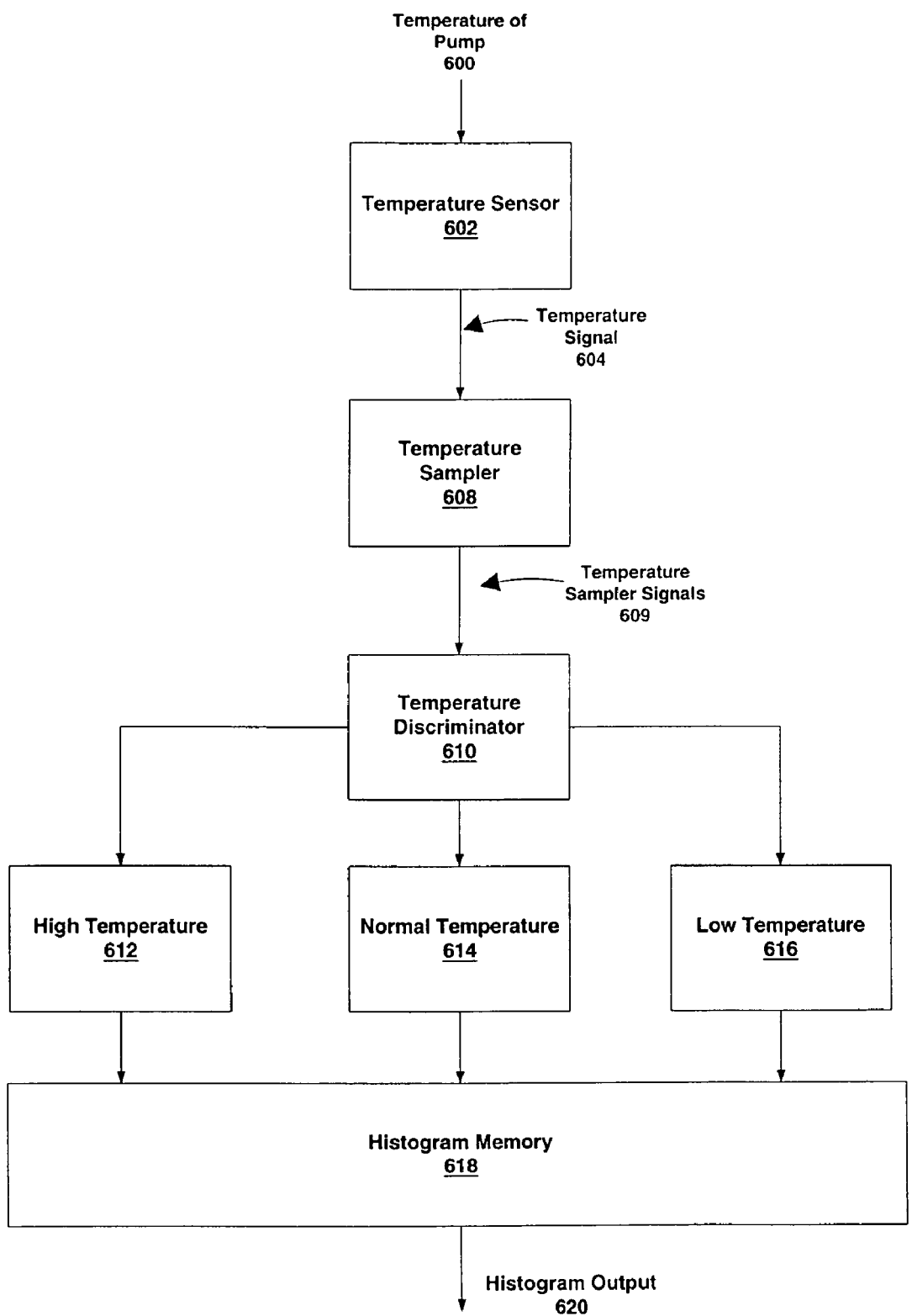
FIG. 6 shows a flow chart depicting the steps needed to produce a histogram output of the total time an implantable pump was exposed to various temperature ranges.

The temperature sensor 150 of FIG. 1 may be used to continuously monitor the temperature of the implantable pump. Alternatively, a temperature sensor placed in the packaging of the pump prior to shipment could be used to monitor the temperature of the implantable pump. FIG. 6 illustrates a flow chart describing a preferred embodiment of the steps for producing a histogram output of the total time an implantable pump is exposed to various temperature ranges. The histogram is one visual form of output a healthcare provider can quickly examine to determine if the implantable pump was exposed to pump damaging temperature extremes. Those skilled in the art will appreciate that other forms of output may also be provided and still be considered within the scope of the invention. For example, the output may be in the form of an audio and/or visual signal. Such a signal may provide a ready indicator to the patient's health care provider (such as a red light or a green light) as to whether the pump is suitable for implant. In this embodiment, the microprocessor within the pump would make the determination based on the data histogram output.

Referring still to FIG. 6, the temperature 600 of the implantable pump as sensed by temperature sensor 602 could be read by a temperature sampler 608 or microprocessor, in the form of an electrical voltage or other electrically measurable quantity such as the resistance of a thermistor. The temperature sampler 608 may continuously monitor the implantable pumps temperature or may be programmed to sample the temperature at predetermined intervals of time. The predetermined sampling interval could be determined by the pump manufacturer and vary depending upon the available memory capacity of the pump. The temperature sampler signals 609 would be input to a temperature discriminator 610 that would separate the signals into three general temperature ranges: high temperature 612, normal temperature 614, and low temperature 616. The temperature ranges could be determined based upon the specified storage temperature range over which the implantable pump can be stored safely and continue to be suitable for patient implantation. Those skilled in the art will understand that numerous temperature ranges could be determined. For example, the temperature ranges could vary in value and number according to the type of drug being used or stored in the pump.

The actual temperatures along with the time, date, and range classifications are stored in histogram memory 618 for later retrieval. The time and date could be recorded with a clock operatively coupled to the temperature sampler 608 or microprocessor. Additionally, the histogram memory 618 may save the accumulated time the temperature has been in the three predetermined ranges. FIG. 5A, illustrates the type of information that is stored in histogram memory 618. This graph shows the temperature profile of the implantable pump over time as monitored by the temperature sensor 602. Prior to pump implant, the healthcare provider receives the stored accumulated time in each of the three temperature ranges, for example, via telemetry from the pump. Optionally, the healthcare provider may display the data for reading as shown in FIG. 5B. The histogram format shown in FIG. 5B is one of several possible data display formats that a healthcare provider can use to assist in interpreting the data.

In another embodiment of the invention, the pump reservoir may be filled with a medicament that is temperature sensitive. For example, the medicament may have a narrow storage temperature range prior to implant of the pump. In this case, the healthcare provider may program the upper and lower temperature limits to a narrower range for the medicament monitoring. If the temperature exceeds the acceptable or normal range, the damaged medicament could be replaced as necessary.

As an additional advantage, manufacturing the pump to monitor its temperature provides another quantum of data that might be useful in the patient's treatment regimen. After installation into a patient, the temperature of the pump 100 will quickly adjust to match the temperature of the body into which it is implanted. Therefore, the pump 100 can also function as a patient temperature probe which tracks patient temperature. Infused medication dosage might be modulated according to a patient's temperature such that as the microprocessor noticed the pump's temperature steadily rising the microprocessor might modulate dosages and/or initiate a communication via the RF link to a health-care provider. Alternatively, as discussed earlier in FIG. 2, a temperature sensor could be placed at the distal tip of the infusion catheter with sensor electrical wire(s) running the length of the catheter and interfacing to the pump via an electrical connector. If the distal tip of the catheter which includes the temperature sensor would be near the body surface it may detect surface or patient-ambient temperature which may not be as therapeutically useful. Therefore, the distal tip of the catheter should be positioned so it could detect the core temperature of a patient. The distal tip position may also be determined by the need to provide a localized infusion of a therapeutic medicament. Advantageously, the sensed temperature of the patient may be used to adaptively administer a drug therapy regimen based on patient temperature.

Figure 8:
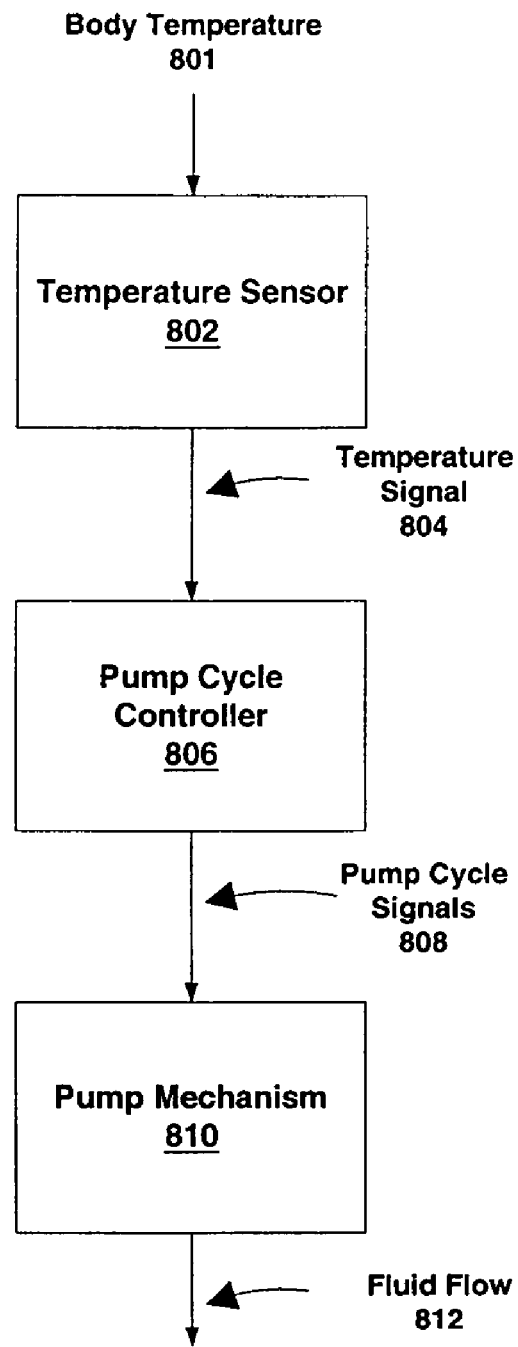
FIG. 8 shows a flow chart depicting the steps needed to produce a flow from an implantable pump dependent on a patient's body temperature.

FIG. 8 depicts a flow chart illustrating the steps for adaptively administering a drug regimen from an implantable pump based on a patient's body temperature to maximize the therapeutic effect of a drug therapy. As shown in FIG. 8, the temperature sensor 802 senses a patient's body temperature 801. The temperature signal 804 is read by the pump cycle controller 806 or microprocessor, in the form of an electrical voltage or other electrically measurable quantity such as the resistance of a thermistor. The pump cycle controller 806 or microprocessor may continuously monitor the patient's body temperature or may be programmed to sample the patient's body temperature 801 at predetermined intervals of time. After reading the temperature signal 804, the pump cycle controller 806 may apply an algorithm that contains a predetermined proportional relationship between pump cycles and a patient's body temperature as depicted in FIG. 7A. Alternatively, the pump cycle controller 806 may apply an algorithm that contains a predetermined proportional relationship between pump flow rate and a patient's body temperature as depicted in FIG. 7B. Based on the predetermined relationship, a pump cycle signal 808 is generated and delivered to the pump mechanism 810 to direct the pump to deliver the proper amount of drug flow 812. The actual patient's body temperature may be stored in one or more storage devices for later retrieval by a healthcare provider using a data link coupled the pump cycle controller 806. Additionally, a clock operatively coupled to the pump cycle controller 806 may be used to generate a signal representative of the time and date of the patient's body temperature.

For example, an implanted pump may continuously or at predetermined intervals sense and store the core or body temperature of a patient. When the sensed temperature increases to a preset value, a low-grade fever is detected which may be therapeutically undesirable. The pump may gradually or abruptly increase the infusion rate, perhaps even providing a bolus infusion, to counteract the low-grade fever. The infused medicament could be a fever reducing medicament or perhaps an antibacterial medicament. The low-grade fever may be a consequence of localized infection or a systemic reason. When the low-grade fever has been reduced or eliminated, the infusion rate may return to a basal rate or cease. The time dependent temperature record could be sent to the healthcare provider by telemetry on demand or automatically. This record would be useful to monitor the effectiveness of the therapy or to help the healthcare provider decide to adjust the infusion rate dependence on a patient's body temperature.

Figure 3:
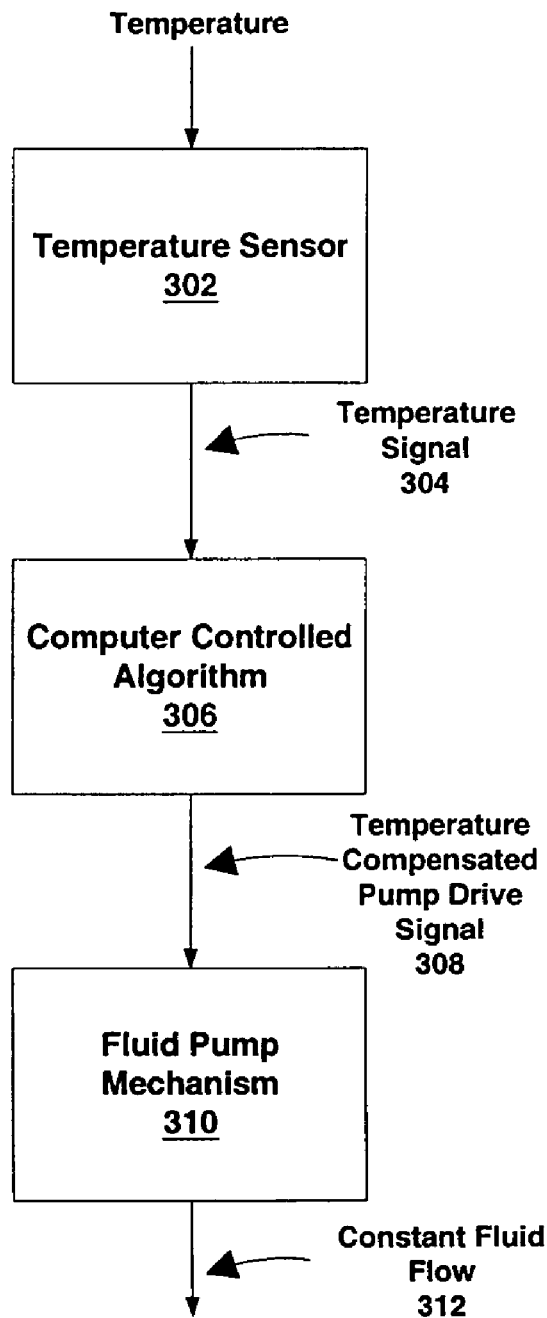
FIG. 3 shows a flow chart illustrating the steps to compensate drug delivery flow in an infusion pump.

In another embodiment of the invention, an infused drug therapy regimen is adaptively administered according to a temperature compensation algorithm that adjusts uncompensated flows for temperature so that a constant flow rate can be achieved. As illustrated in FIG. 3, a temperature sensor 302 would be read by the microprocessor 306 in the form of an electrical voltage or other electrically measurable quantity such as the resistance of a thermistor. The temperature signal 304 would be read into the controller 306 where an algorithm would be used to determine whether the uncompensated flow should be temperature compensated. If the controller 306 determines that a correction to the uncompensated flow is needed, then a temperate compensated pump drive signal 308 is delivered to the pump 310 to produce from the pump a constant fluid flow rate 312. The temperature compensation algorithm as illustrated in FIG. 4B shows a predetermined relationship between pump cycles and temperature. As the uncompensated flow rate changes with temperature, FIG. 4A, the temperature compensation algorithm adjusts the flow rate to provide a constant flow rate as illustrated in FIG. 4C.

An example of a temperature dependent flow rate can be found in the propellant flow from a propellant pump. Monitoring a pump propellant's temperature using a temperature probe allows the controller to compensate drug delivery for the propellant's pressure-temperature dependence and hence the propellant's temperature. As gaseous propellant changes temperature, its effectiveness in delivering drug therapy will also change. Accordingly, by monitoring the propellant's temperature, the microprocessor or other control circuitry can adjust the drug delivery appropriately to provide for a constant fluid flow delivery of the therapeutic.

While the invention has been described with respect to specific examples including presently preferred mode of carrying out the invention, those skilled in the art will appreciate that there are numerous variation and permutations of the above described systems and techniques that fall within the spirit an scope of the invention as set forth in the appended claims and their equivalents.

We claim:

1. An automatic drug therapy delivery system, capable of detecting the possibility of damage to the pump prior to implant, the system comprising:
   a) an implantable pump;
   b) a temperature sensor producing electrically measurable signals that are indicative of the temperature of the implantable pump over time prior to implantation; and
   c) a controller having at least one input that receives the signals from the temperature sensor, wherein the controller monitors the signals from the temperature sensor prior to implantation of the implantable pump and stores those signals from the temperature sensor that are indicative of the implantable pump being exposed to a temperature that is one or more of inside or outside of a pre-determined normal range at which the implantable pump can be safely stored.

2. The automatic drug delivery system of claim 1, wherein the controller comprises a microprocessor.

3. The automatic drug delivery system of claim 2, wherein the microprocessor further provides an indication regarding the suitability of implanting the implantable pump based on the signals received from the temperature sensor.

4. The automatic drug therapy delivery system of claim 3, wherein the indication provided by the microprocessor comprises an audio signal.

5. The automatic drug therapy delivery system of claim 3, wherein the indication provided by the microprocessor comprises a visual signal.

6. The automatic drug delivery system of claim 1, wherein the controller generates a temperature profile from the signals, the temperature profile being retrievable to detect a possible pump damaging temperature, and wherein the temperature profile comprises a histogram.

7. The automatic drug delivery system of claim 6, wherein the histogram comprises ranges of high temperature, normal temperature, and low temperature.

8. The automatic drug delivery system of claim 6, further comprising a data link coupled to the controller for the retrieval of the temperature profiles.

9. The automatic drug delivery system of claim 6, further comprising at least one storage device for storing the temperature profile.

10. The automatic drug delivery system of claim 6, further comprising a plurality of memory storage locations wherein the temperature profile of the implantable pump is stored.

11. The automatic drug therapy delivery system of claim 6, wherein the controller further generates the temperature profile that provides information about an accumulated time that the implantable pump was exposed to corresponding to the at least one abnormal temperature range.

12. The automatic drug therapy delivery system of claim 6, further comprising:
   a pump reservoir that connects to the implantable pump and that contains a medicament, the medicament being temperature sensitive; and
   wherein the controller generates the temperature profile that is retrievable to detect a possible medicament damaging temperature.

13. The automatic drug delivery system of claim 1, further comprising a clock, operatively coupled to the controller, the clock generating an output signal representative of time and date.

14. The automatic drug delivery system of claim 1, wherein the at least one abnormal temperature range is below the normal temperature range.

15. The automatic drug delivery system of claim 1, wherein the controller is configured to provide an indication of the amount of time that the implantable pump was exposed to a temperature outside of the normal temperature range.

16. An automatic drug therapy delivery system, capable of detecting the possibility of damage to the pump prior to implant, the system comprising:
   a) an implantable pump;
   b) a temperature sensor producing electrically measurable signals that are indicative of temperature to which the implantable pump is subjected prior to implantation; and
   c) a controller having at least one input that receives the signals from the temperature sensor, the controller monitoring and recording the signals from the temperature sensor prior to implantation, the controller further including a discriminator to separate the received signals into categories representing one of three pre-determined temperature ranges, the three temperature ranges comprising a below normal temperature range, a normal temperature range and an above normal temperature range.

17. The automatic drug delivery system of claim 16, wherein the controller is configured to make the determination of which temperature range the signal corresponds to while the implantable pump is not in operation.

18. The automatic drug delivery system of claim 16, wherein the controller is configured to make the determination of which temperature range the signal corresponds to prior to the implantable pump being implanted within a patient.

19. The automatic drug delivery system of claim 16, wherein the controller is a microprocessor.

* * * * *